United States Patent [19]

Uramoto

[11] 4,320,291

[45] Mar. 16, 1982

[54] OPTICAL INSTRUMENT

[75] Inventor: Hiromu Uramoto, Takatsuki, Japan

[73] Assignee: Yuasa Battery Company Limited, Takatsuki, Japan

[21] Appl. No.: 99,823

[22] Filed: Dec. 3, 1979

Related U.S. Application Data

[63] Continuation-in-part of Ser. No. 967,985, Dec. 11, 1978, abandoned, which is a continuation-in-part of Ser. No. 804,298, Jun. 1, 1977, abandoned.

[30] Foreign Application Priority Data

Oct. 20, 1976 [JP] Japan .................................. 51-126628

[51] Int. Cl.³ .............................................. G02B 5/14
[52] U.S. Cl. .................................... 250/227; 250/578; 356/136
[58] Field of Search ................ 250/227, 577; 356/135, 356/136, 137; 73/293

[56] References Cited

U.S. PATENT DOCUMENTS 3,384,885  5/1968  Forbush ............................. 250/557
3,553,666  1/1971  Melone ............................... 250/227
3,751,672  8/1973  Michel et al. ...................... 356/136
3,932,038  1/1976  Schweizer et al. ................. 356/135
3,977,790  8/1976  Schweizer et al. ................. 356/136

Primary Examiner—David C. Nelms
Attorney, Agent, or Firm—Watson, Cole, Grindle & Watson

[57] ABSTRACT

An optical instrument for measuring the specific gravity of a solution, particularly the specific gravity of the acid in a lead acid battery, which incudes a base part and a transparent member, the transparent member including an incident light surface and reflector. The instrument further includes a light source arranged in the base part of the transparent member which is capable of radiating a straight-lined ray into the transparent member parallel to the axis of the member, and a photosensitive element for receiving light reflected by the incident light surface and the reflector. During use the instrument is positioned such that the transparent member is in contact with the solution whose specific gravity is to be measured.

12 Claims, 8 Drawing Figures

OPTICAL INSTRUMENT

CROSS REFERENCE TO RELATED APPLICATIIONS

This application is a continuation-in-part application of application Ser. No. 967,985 filed Dec. 11, 1978, now abandoned, which in turn was a continuation-in-part application of application Ser. No. 804,298, filed June 1, 1977, now abandoned.

BACKGROUND OF THE INVENTION

1. Field of the Invention

The present invention relates to optical instruments for measuring the density of a solution.

2. Description of the Prior Art

Refractometers for measuring the refractive indexes of liquids, such as, for example, Abbe-type or Pulfrich-type refractometers, are well known. When using such refractometers, one surface of a transparent member having a known refractive index is brought into contact with a solution to be examined a light is directed towards the surface of the transparent member and its angle of refraction is measured to determine the refractive index. However, these refractometers are not entirely satisfactory since the steps for their use are complicated, involving collecting a fixed amount of the solution to be examined, maintaining the solution stationary and calculating the index. In addition, when the refractive index of the solution varies with time or is converted to an electric signal which is detected by remote control, accurate measurement of the index can be very difficult.

Another known apparatus for measuring the density of liquids by determining the refractive index is disclosed in U.S. Pat. No. 3,977,790 to Schweizer et al. The apparatus utilizes a divergent light ray radiated from a light source into a light-conductive rod, the light ray being non-parallel with the longitudinal axis of the light-conductive rod. When the divergent ray reaches a measuring or incident surface of the rod, the light ray is diffused so as to utilize the total reflection angle on the measuring surface. Therefore, the fact that the light ray is non-parallel with the axis of the rod is advantageous since the light ray can be applied to the measuring surface in a wide range.

An object of the present invention is to eliminate the above-mentioned problems with conventional refractometers.

Another object of the present invention is to provide an optical instrument wherein an accurate measurement of the specific gravity of a solution can be obtained by a relatively easy operation.

Yet another object of the present invention is to provide an optical instrument which is simple in structure and low in cost.

A further object of the present invention is to provide an optical instrument adaptable to a variety of uses.

SUMMARY OF THE INVENTION

In its broader aspects, the present invention comprehends an optical instrument for measuring the specific gravity of a solution which comprises an elongated transparent member, a photosensitive element and a light emitting element located at one end of the transparent member to respectively receive or send light through the transparent member, an incident light surface located at the opposite end of the transparent member and oriented so as to be inclined with respect to the incident rays of light directed thereagainst from the light-emitting element, and a reflector surface located adjacent to the incident light surface and oriented so as to be capable of reflecting the reflected light from the incident light surface to the photosensitive element in parallel with the light emitted from the light source. In operation the optical instrument is immersed in the solution whose specific gravity is to be measured such that the external surface of the incident light surface is in contact with the solution, the light incident thereon being divided into a light portion which enters the solution and a light portion which is reflected towards the reflector surface, this reflected light being then 100% reflected towards the photosensitive element to allow for a determination of the specific graivty of the solution from the received light flux.

The present invention will be more easily understood by referring to the following drawings and description.

DETAILED DESCRIPTION OF PREFERRED EMBODIMENTS

Figure 1A:
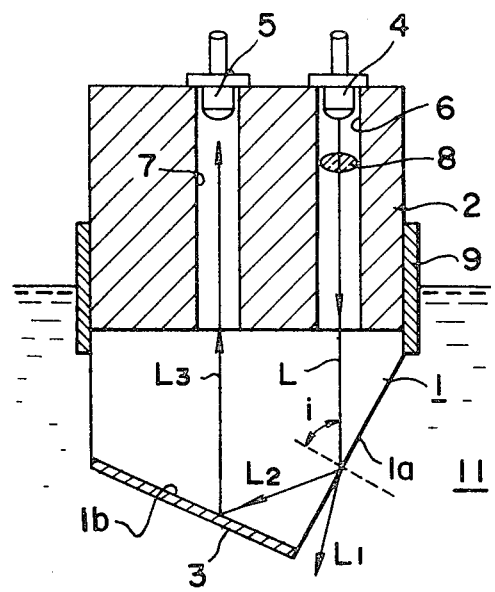
FIGS. 1A and 1B show explanatory views of embodiments of optical instruments according to the present invention.

In FIG. 1A, which shows a first embodiment of optical instrument according to the present invention, the instrument body consists of a transparent glass member 1 and an elongated base part 2 made of a synthetic resin, the glass member 1 having an incident light interface 1a and a reflective interface 1b at the tip which together enclose an angle of about 90 degrees, a mirror 3 being fitted to the reflective interface 1b so as to reflect 100% of the light striking its surface. The incident light interface 1a and the reflective interface 1b each have flat surfaces. The mirror 3 is formed by securing a film of, e.g., aluminum, silver or gold to the glass member by vapor deposition. A light source 4 consisting of a light-emitting diode or the like is located in the upper portion of the elongated base part 2 so as to emit, when activated by electric power fed from an electric power source (not illustrated), light towards incident light interface 1a. Further, a photosensitive element 5 consisting of a phototransistor is arranged in parallel with the light source 4 in the upper portion of the base part 2. Light from the light source 4 may be partly reflected by the incident light interface 1a and may reach the reflective interface 1b, and further the light reflected by this interface 1b may be directed in parallel with the light directed toward the incident light interface 1a. Also, it is a requirement that the light should have as little expansion as possible so that an accurate measurement may be possible. In the drawing, a first through-hole 6 in the base part 2 provides a passageway for the light from the light source 4 to pass towards interface 1a, and a second through hole 7 provides a passageway for the reflected light from interface 1b to pass towards the photosensitive element 5. A paralleling lens 8 for reducing expansion in the light emitted from the light source 4 is located in the through-hole 6. A protective material 9 surrounds the base part 2 for preventing solution from entering the glass member 1 at its point of connection with the base part 2.

Figure 1B:
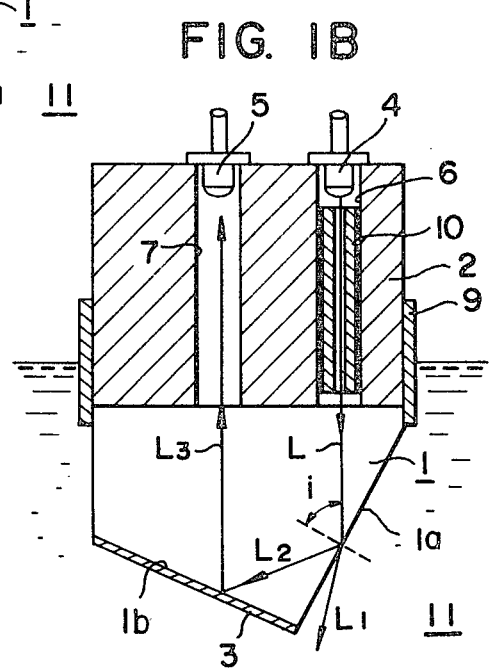

In FIG. 1B, which shows another embodiment of the present invention, a tubular light-limiting limiting path member 10 is located in the through-hole 6 on the light source 4 side which is made of a non-transparent material as, for example, a synthetic resin or ceramic. This member 10 has a diameter somewhat smaller than that of the through-hole 6 and it includes a fine hole along its axis.

In operation, either of the instruments shown in FIGS. 1A or 1B are about half dipped in a solution 11 to be examined. The light L radiated from the light source 4 will pass through the transparent member to reach the incident light interface 1a at an incident light angle i and will be divided. One divided light portion $L_1$ will be incident upon the solution 11 to be examined. The other divided light portion $L_2$ will be internally reflected within the transparent member 1. Further, the light $L_3$ reflected by the reflector 3 will be directed back to the photosensitive element 5. In case the incident light angle is close to 90 degree, the light flux of the reflected light portion $L_2$ will be represented by the following formula by the law of general light reflection:

$$L_2 = K \cdot L_V \cdot \left( \frac{1 - \frac{n_B}{n_A}}{1 + \frac{n_B}{n_A}} \right)^2$$

wherein

K is a constant determined by the incident angle i,
$L_V$ is a total light flux radiated from the light source,
$n_A$ is a refractive index of the transparent member and
$n_B$ is a refractive index of the solution to be examined.

Figure 2:
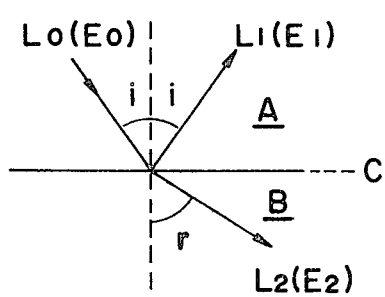
FIG. 2 shows a drawing which explains the principle of the optical instrument of the present invention.

FIG. 2 can be used to explain the general principle of the present invention. When a light $L_O$ having an energy $E_O$ is projected at an incident light angle i upon an interface C with a substance B having an optical refractive index $n_B$ through a substance A having an optical refractive index $n_A$, the light $L_O$ will be divided into a reflected light portion $L_1$ having a reflection angle i and a refracted light portion $L_2$ having a refraction angle r. As a result of theoretical considerations, it is found that if the respective energies are $E_1$ and $E_2$, the relation of the following formulas will be established:

$$\begin{cases} \frac{E_1}{E_2} = \frac{\sin^2(i-r)}{\sin^2(i+r)} + \frac{\tan^2(i-r)}{\tan^2(i+r)} \\ E_0 = E_1 + E_2 \end{cases}$$

By the above formulas, if i is constant, $E_1$ will vary with only the refraction angle r by the substance B. Theoretically this means that the refractive index of the substance B can be found by measuring the energy $E_2$ at a photosensitive point at which a non-divergent straight-lined finely throttled beam-shaped light is arranged symmetrically with the normal.

Now, in case an optical glass of a refractive index of 1.512 is used for the transparent member and sulfuric acid solution having differing specific gravities is used for the solution to be examined, the incident light angle based on the critical angle calculation will be as follows:

TABLE 1

| Curve | A | B | C | C |
|---|---|---|---|---|
| Incident light angle i | 61.60° | 63.32° | 64.71° | 65.96° |
| Specific gravity value of sulfuric acid | 1.000 | 1.100 | 1.200 | 1.300 |
| Refractive index | 1.333 | 1.351 | 1.367 | 1.381 |

In the curves A, B, C and D, the incident light angle i is so determined that a total reflection may be made at each of the specific gravity values of 1.000, 1.100, 1.200 and 1.300.

Figure 3:
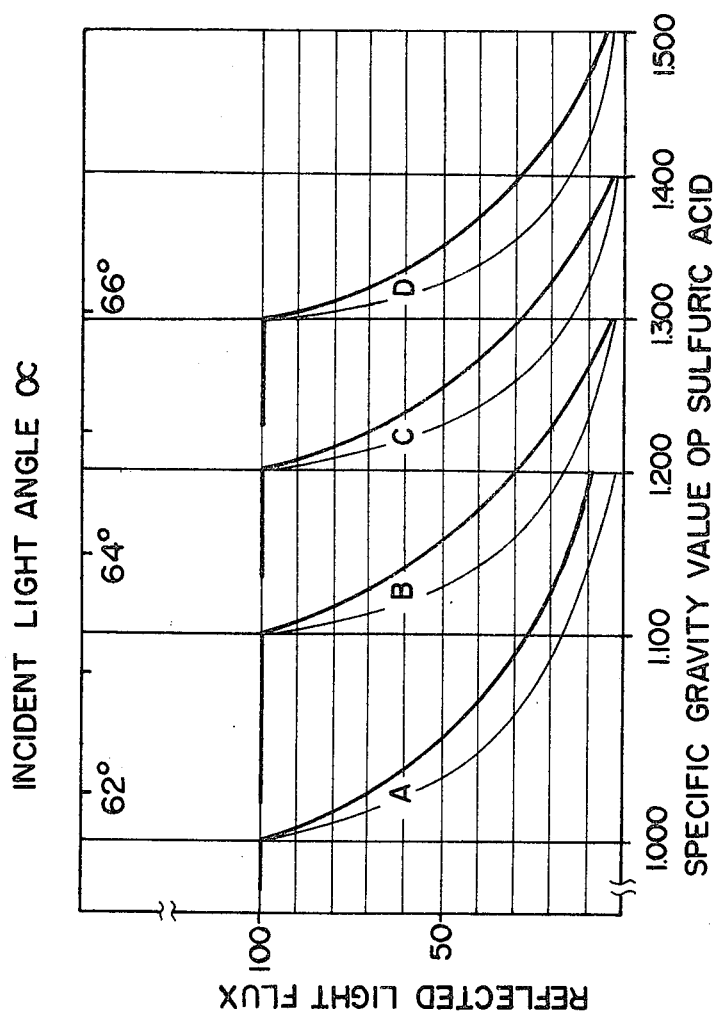
FIG. 3 shows interrelation curves of incident light angles, reflected light fluxes and specific gravities of sulfuric acid.

One curve A will now be described in detail. When an optical instrument of the present invention in which the incident light angle i has an incident light interface of 61.60 degrees is used, if various measurements are made by varying the specific gravity of the sulfuric acid, at a specific gravity of 1.000 the reflected light flux will be maximum in the total reflection. If this is given a value of 100, the reflected light flux will reduce to 25 at a specific gravity of 1.100 and to 10 at a specific gravity of 1.200. That is to say, with an increase in the specific gravity value, the reflected light flux will decrease. The curve A in FIG. 3 shows this relation. The curves B, C and D are obtained in the same manner as curve A and show the same relations.

Figure 4:
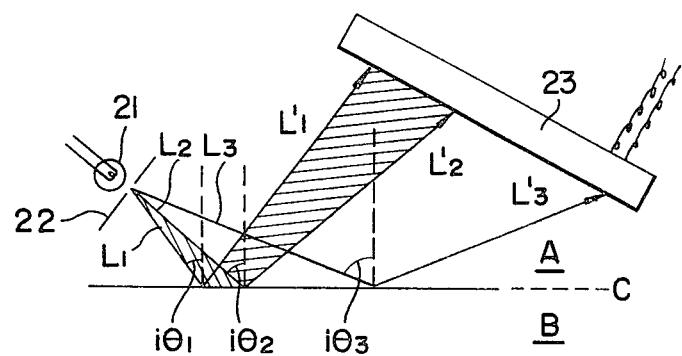
FIG. 4 depicts the measuring principle of a conventional optical instrument, i.e., as described in U.S. Pat. No. 3,977,790 to Schweizer et al.

FIG. 4 is an explanatory view showing the principle of U.S. Pat. No. 3,977,790 to Schweizer et al. As described above, in the above U.S. patent a total reflection phenomenon of a light on an interface is utilized by using a divergent ray. That is to say, a light coming out of a light source 21 will become a light having an expansion from $L_1$ to $L_3$ when passing through a slit 22, it will pass through a transparent member A and it will enter an interface C with a substance B to be measured. There, the light will become a light having light fluxes of reflected lights $L'_1$ and $L'_3$, which will be received on a photosensitive surface 23 and will be transmitted as an electric signal. It is well known that, in such case, the incident light angle i of the interface C with the normal can be made to make a total reflection by properly selecting the transparent member A and the optical refractive indexes $n_A$ and $n_B$ of the substance to be examined. In such case, the incident light angle is called a total reflection angle or critical angle and is represented by the following formula:

$$i_\theta = (n_B/n_A)$$

where $i_\theta$ is a critical angle and $n_A > n_B$.

FIG. 4 shows the manner in which the optical refractive index of the substance to be examined varies from $n_{B1}$ to $n_{B3}$ and thereby the critical angle varies from $i_{\theta 1}$ to $i_{\theta 3}$. In case $n_B$ is of an intermediate value $n_{B2}$, the light between the critical angles $i_{\theta 2}$ and $i_{\theta 3}$ will be reflected by the total reflection but the other lights than it will be absorbed into the substance B as refracted lights and will not be projected on the photosensitive surface 23.

The hatched portion means a light flux not projected. At the time of $n_{B3}$, the light flux will be of a minimum value and, at the time of $n_{B1}$, the light flux will show a maximum value. It is the measuring principle of the above-mentioned U.S. patent to measure the optical refractive index of $n_B$ by measuring the width of this projected light flux. Therefore, it is required that the light projected on the interface should have an expansion width large enough to cover at least the abovedescribed critical angle variation range. By the way, as the specific gravity variation range in a sulfuric acid lead battery is about 1,000 to 1,320, the projected light flux must have a critical angle width of at least 61 to 66 degrees (as calculated by using the glass member having a light refractive index of 1.516 as a transparent member).

In the present invention, in order to elevate the measuring precision, it is preferable to make the light from the light source a beam light, that is, a non-divergent straight-lined ray as much as possible. Thus, the light from a general light-emitting diode having an expansion width of about 10 degrees is reduced to an expansion of 0.5 degree by the paralleling lens 8 in FIG. 1A. Alternately, as shown in FIG. 1B, the expansion component of the light can be reduced by passing the light for a fixed distance through a pinhole or a slit extending through the light-emitting path member 10. The following formula is shown by a passing distance L and pinhole diameter d of the light-emitting path in member 10:

$$\tan \theta = d/L$$

In case $d/L=0.1$, $\theta=5.7°$.
In case $d/L=0.02$, $\theta=1.14$.
The light passing through such light-limiting path will be considerably reduced in its expansion.

When experimentally confirmed, in the case of the parallelization by using a convex lens of a diameter of 5 mm and focal length of 20 mm, the expansion width is reduced to 0.5 degree without reducing the effective light flux. Further, in the case of a lens of a diameter of 5 mm and focal length of 12 mm, the expansion width was 0.8 degree. The parallelism was further improved by using semiconductor laser or gas laser rays for the light source but there are defects in the size and price. These are all confirmed to operate without trouble for the measurement of the refractive index of the sulfuric acid electrolyte. Experimentally it is preferable that $\theta$ is not more than 1.5 degrees. If $\theta$ exceeds 1.5 degrees, the light expansion will become large and the measuring precision will deteriorate. It is confirmed by experiments that if $\theta$ is not more than 1.5 degrees, the decomposability in the case of measuring the specific gravity will be about 0.002, but at 2.5 degrees it will be ±0.005 and at 4 degrees it will increase to about ±0.014. In the case of utilizing a light-limiting path, L will be 2 to 35 mm and d will be preferably in the above-mentioned $\theta$ range. By the way, the refractive index of the glass member is required to be above 1.5. If it is not above 1.5, the measuring range will become narrow and the precision will decrease. This requirement is important particular in the measurement of the specific gravity of the electrolyte of sulfuric acid battery. The transparent member can be made of not only glass, but also of a synthetic resin. However, a methacrylic resin will be attacked by sulfuric acid on the interface, which will influence the refractive index, and thus such a resin cannot be used. Vinyl chloride, polycarbonate and polyvinylidene chloride can be used as transparent materials, these being acid proof and at the same time displaying the above-mentioned refractive index.

|  | Refractive index | Transparency |
| --- | --- | --- |
| Vinyl chloride | 1.54 | 70 to 90% |
| Polycarbonate | 1.58 | 93 to 95% |
| Polyvinylidene chloride | 1.60 | 50 to 70% |

Figure 5:
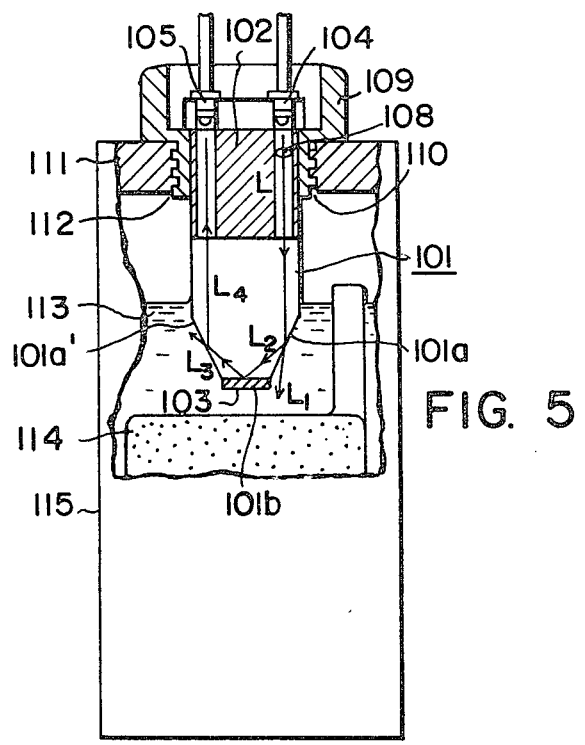
FIG. 5 shows a further embodiment of optical instrument according to the present invention.

FIG. 5 shows another modification of the present invention. It is positioned particularly into a lead acid battery and is adapted to measure the specific gravity of the electrolyte or to measure the charge or discharge of the battery. It is fixedly connected with a base part 102 made of a synthetic resin or the like. A reflector 103 is provided at the tip 101b of the transparent member 101 in the same manner as in the device in FIG. 1. A light source 104 and photosensitive element 105 are arranged in parallel with each other in the upper portion of the base part 102. The base part is provided with throughholes 106 and 107. A paralleling lens 108 is arranged particularly within the through hole 106 on the light source 104 side. This device body is fitted to an annular sleeve 109 which is screwed into a female screw 112 of the lid of the lead acid battery with a male screw 110 on the outer periphery of the annular sleeve 109. In operation, the tip of the transparent member is dipped in the electrolyte 113 consisting of sulfuric acid of a required specific gravity. A plate 114 of the lead acid battery is contained together with the electrolyte 113 in a battery container 115.

Now, a light L radiated from the light source 104 will reach the first incident light interface 101a and will be divided into a light portion $L_1$ entering the electrolyte 113 and a reflected portion $L_2$. This light portion $L_2$ will be reflected by the reflector 103, will reach the second incident light interface $101a'$ and will be divided into a light portion $L_3$ entering the electrolyte 113 and a reflected light portion $L_4$. The light portion $L_4$ will further reach the photosensitive element 5. Its light flux is represented by the following formula:

$$L_4 = L \times \left( \frac{\tan^2 (i - r)}{\tan^2 (i + r)} + \frac{\sin^2 (i - r)}{\sin^2 (i + r)} \right)^2$$

wherein
i is an incident light angle on the incident light interface of the light L and
r is a refraction angle in the electrolyte of $L_1$ and $L_3$.

As described above, the light flux of the light portion $L_4$ reaching the photosensitive element 105 will vary correlatively with the specific gravity value of the sulfuric acid of the electrolyte 113.

Now, the relation between the specific gravity value of the sulfuric acid and the light current shown by the photosensitive element is as follows:

TABLE 2

| Specific gravity value of sulfuric acid | 1.100 | 1.150 | 1.200 | 1.250 | 1.300 |
| --- | --- | --- | --- | --- | --- |
| Light current (mA) | 1.50 | 1.12 | 0.80 | 0.48 | 0.35 |

The above-described modification applying the optical instrument of this embodiment to a lead acid battery has the following further advantages.

As the incident light interfaces of the transparent member are plural, the rate of reduction of the light reaching the photosensitive element will be large. As a result, any minute variation of the specific gravity of the sulfuric acid can be detected more easily. As the incident light interfaces are formed to be sloped, during the use of the lead acid battery, generated oxygen and hydrogen gases will not be deposited on the sloped incident light interfaces. As a result, gases will not be deposited on the incident light interfaces, the light will not be temporarily disturbed and that the measured value will not be abnormal. However, as required, i.e., so that no gas may be deposited on the incident light interface, there may be provided either a shielding plate between the plates or a cleaning means on the incident light interface. Further, it is well known that a lead acid battery will show a perfect discharge when the specific gravity of the sulfuric acid of the electrolyte is about 1.150 and a perfect charge at about 1.280. However, by a special using method, it may be expanded to be about 1.020 at the end of the discharge and about 1.320 at the end of the charge. In case the optical instrument of the present invention is thus applied to a lead acid battery, there will be able to be easily known the specific gravity value of the sulfuric acid from the above described reflected light flux and the charge or discharge through it. It is an inherent advantage as applied to a lead acid battery.

Figure 6:
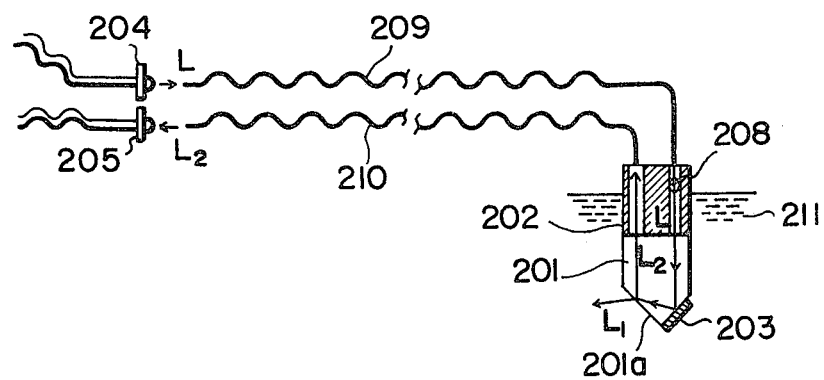
FIG. 6 depicts another embodiment of optical instrument according to the present invention.

FIG. 6 shows another modification of the present invention. An optical instrument is shown wherein a transparent member 201 and base 202 are connected with a light source 204 and photosensitive element 205 through respective optical fiber cords 209 and 210 made of glass much to the advantage of remotely measuring a solution. Its operation will be as follows: A light L radiated from the light source 204 to the transparent member 201 via a luminous optical fiber cord 209 and a paralleling tens 208 will be reflected by a reflector 211, then it will reach an incident light interface 201a and then it will be divided into a light portion $L_1$ entering the solution 211 to be examined and a reflected light portion $L_2$ reflected by the incident light interface 201a. The reflected light portion $L_2$ will reach the photosensitive element 205 through the luminous optical fiber cord 210. The light flux of this reflected light portion $L_2$ will be displayed by a meter or digits through an amplifier. Thus the specific gravity of the electrolyte and the charge or discharge of the lead acid battery can be remotely measured. As a result, there is an inherent advantage that the maintenance of the lead acid battery is easier.

Figure 7:
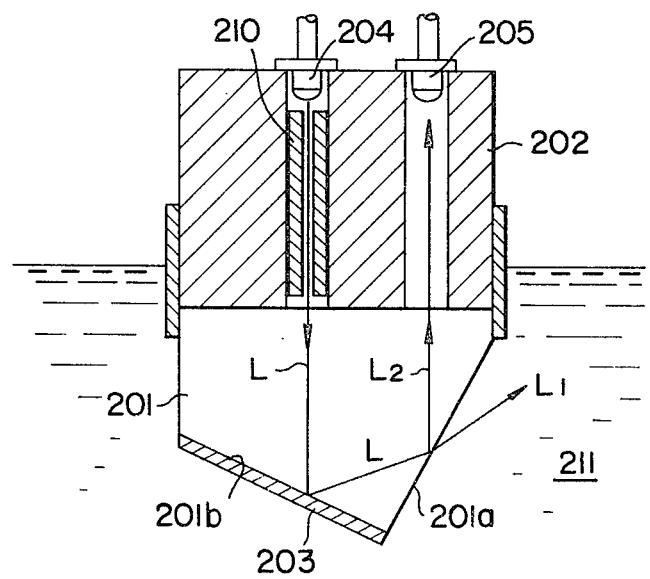
FIG. 7 shows a still further embodiment of optical instrument according to the present invention.

FIG. 7 shows still another modification of the present invention. A light L coming out of the light source 204 will pass through a light-limiting path 210 and will be reflected by the reflective interface 201b of the transparent member 201. On the incident light interface 201a, a portion of the light L will advance as a light $L_1$ into the electrolyte 211 and the other portion $L_2$ of the light L will be reflected and, will advance through the transparent member 201 and will be received by the photosensitive element 205 in the base part 202. In this modification, the light from the light source will be reflected by the reflective interface and then will be applied to the incident light interface. Therefore, the measurement can be made.

As further another modification, the light-limiting path may be brought before the photosensitive element. However, in this manner, the effective light flux will decrease.

It goes without saying that the optical instrument of the present invention can be used to not only measure the specific gravity of the acid in a lead acid battery but also to measure the characteristics of other solutions as well, for example, to determination the concentration of an aqueous solution of caustic soda or common salt, a petroleum distillate or a transformer oil.

Other modifications of the present invention are also possible without departing from the spirit of the present invention. For example, though the optical instrument of the present invention can be constructed so as to be fixed to the lead acid battery, it is not limited to this construction but instead it can be constructed as a a portable transparent member to be dipped by hand into an electrolyte in case it is only necessary to measure the electrolyte.

Further, it goes without saying that whether the light radiated from the light source will reach the reflector through the incident light interface of the transparent member or will reach the incident light interface through the reflector can be freely selected and designed.

While the present invention has been described with reference to particular embodiments thereof, it will be understood that numerous modifications may be made by those skilled in the art without actually departing from the spirit and scope of the invention as defined in the appended claims.

I claim:

1. An optical instrument for measuring the specific gravity of a solution, said instrument comprising
    an elongated base body having a first end and a second end,
    a light-emitting means located near said first end of the elongated base body for emitting a ray of nondivergent light through the elongated base body,
    a photosensitive element located near said first end of the elongated base body for sensing light passing through the elongated base body in parallel with said ray of nondivergent light emitted by said light-emitting means, and
    a transparent glass member having a refractive index value of not less than 1.5 sealingly connected to said second end of the elongated base body, said glass member including only two light-contacting surfaces which consist of (a) an incident light surface which is positioned and inclined such that said ray of non-divergent light emitted from said light-emitting means will strike the incident light surface and be divided into a light portion entering the solution in which the optical instrument is partly immersed and a reflected portion, and (b) a reflector surface; said reflector surface including a reflective coating enabling 100% of the light hitting said reflector surface to be redirected towards said photosensitive element in a direction parallel to the ray of non-divergent light emitted from said light-emitting means.

2. The optical instrument as claimed in claim 1, wherein said elongated base member includes two parallel passageways therethrough, one for the passage of said ray of nondivergent light emitted from said light-emittting means towards said incident light surface and one for the passage of the light reflected from said reflector surface towards said photosensitive element.

3. The optical instrument as claimed in claim 2, wherein a light ray-limiting means is positioned in the passageway through which the ray of non-divergent light from said light-emitting means passes.

4. The optical instrument as claimed in claim 3, wherein said light ray-limiting means comprises a focusing lens.

5. The optical instrument as claimed in claim 3, wherein said light ray-limiting means comprises a tubular member.

6. The optical instrument as claimed in claim 3 wherein said light ray-limiting means controls the divergence of the ray of light passing therethrough such that it has an expansion angle of not more than 1.5°, the optical instrument being thereby adapted to measure a specific weight of about 1.000 to 1.320 of sulfuric acid.

7. An optical instrument for measuring the specific gravity of a solution, said instrument comprising
an elongated base body having a first end and a second end,
a light-emitting means located near said first end of the elongated base body for emitting a ray of non-divergent light through the elongated base body,
a photosensitive element located near said first end of the elongated base body for sensing light passing through the elongated base body in parallel with said ray of non-divergent light emitted by said light-emitting means, and
a transparent glass member having a refractive index value of not less than 1.5 sealingly connected to said second end of the elongated base body, said glass member including only two light-contacting surfaces which consist of (a) a reflector surface which is positioned and inclined such that said ray of non-divergent light emitted from said light-emitting means will strike the reflector surface, and (b) an incident light surface positioned such that the light reflected by said reflector surface will strike the incident light surface and be divided into a light portion entering the solution in which the optical instrument is partly immersed and a reflected portion which is directed towards said photosensitive element in parallel with the ray of non-divergent light emitted from said lightemitting means; said reflector surface including a reflective coating enabling 100% of the light hitting said reflector surface to be redirected towards said incident light surface.

8. The optical instrument as claimed in claim 7, wherein said elongated base member includes two parallel passageways therethrough, one for the passage of said ray of nondivergent light emitted from said light-emitting means towards said reflector surface and one for the passage of the light reflected from said incident light surface towards said photosensitive element.

9. The optical instrument as claimed in claim 8, wherein a light ray-limiting means is positioned in the passageway through which the ray of non-divergent light from said lightemitting means passes.

10. The optical instrument as claimed in claim 9, wherein said light ray-limiting means comprises a focusing lens.

11. The optical instrument as claimed in claim 9, wherein said light ray-limiting means comprises a tubular member.

12. The optical instrument as claimed in claim 8 wherein said light ray-limiting means controls the divergence of the ray of light passing therethrough such that it has an expansion angle of not more than 1.5°, the optical instrument being thereby adapted to measure a specific weight of about 1.000 to 1.320 of sulfuric acid.

* * * * *